United States Patent [19]

Silvestrini et al.

[11] 4,307,095

[45] Dec. 22, 1981

[54] METHOD OF TREATING SCHIZOPHRENIA WITH CYCLOALKLTRIAZOLES

[75] Inventors: Bruno Silvestrini; Leandro Baiocchi, both of Rome, Italy

[73] Assignee: Aziende Chimiche Riunite Angelini Francesco A.C.R.A.F. S.p.A., Italy

[21] Appl. No.: 182,426

[22] Filed: Aug. 29, 1980

Related U.S. Application Data

[62] Division of Ser. No. 25,273, Mar. 29, 1979, Pat. No. 4,252,721.

[30] Foreign Application Priority Data

Apr. 18, 1978 [IT] Italy ................................ 22421 A/78

[51] Int. Cl.³ .......................................... A61K 31/495
[52] U.S. Cl. .................................................... 424/250
[58] Field of Search .......................................... 424/250

*Primary Examiner*—Stanley J. Friedman
*Attorney, Agent, or Firm*—McGlew and Tuttle

[57] ABSTRACT

Compounds of the general formula:

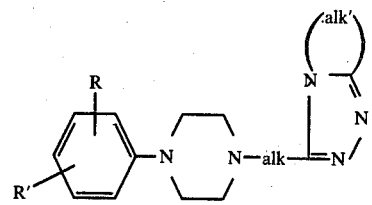

in which alk and alk' represent the bivalent radicals aliphatic alkyl chains; and R and R' represents the alkyl, halogen, hydrogen, alkyloxy, —OH, —CF₃ or —SCH₃ radicals. The compounds of the formula I are, effective as antiglaucomic, antipsychotic and also as additive agents in the withdrawal treatment of various addictive conditions. Methods for their preparation are also disclosed.

8 Claims, No Drawings

METHOD OF TREATING SCHIZOPHRENIA WITH CYCLOALKLTRIAZOLES

This is a division of application Ser. No. 25,273 filed Mar. 29, 1979 now U.S. Pat. No. 4,252,721.

SUMMARY OF THE INVENTION

The present invention relates to new compositions useful as antiglaucomic and antipsychotic agents and also useful as additive agents in the withdrawal treatment of patients from the condition of psychophysical dependence from alcohol, smoke or pharmaceutical products. It also relates to new methods of using these new compositions to treat conditions characterized by the hypertensive state of the eye (including glaucoma), delirium, hallucination and other symptoms of the psychosis of the schizophrenic type. The new compositions are also useful in the treatment of abstinence syndromes in patients with states of psychophysic addiction or dependence on alcohol, smoke and various pharmaceutical products (including narcotic products having analgesic properties). The present invention relates further to new pharmaceutical products which are useful in achieving the aforementioned objects, as well as to methods for their preparation, and to some new intermediates of these products and also to pharmaceutically acceptable salts of the new products. These new compositions comprise 5-substituted derivatives of the 3,4-cycloalkyl triazoles and are represented by the formula I:

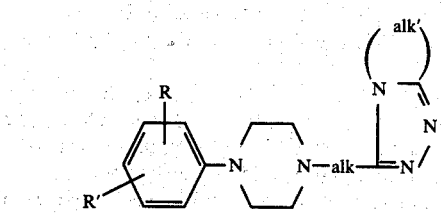

In this formula, the symbol "alk" represents a linear or branched bivalent aliphatic chain having from 1 to 10 carbon atoms. The symbol alk represents a linear or branched aliphatic chain having from 1 to 5 carbon atoms. R and R' (in the cases other than when R=R'=H) represent two substituents on the aromatic nucleus, which may be the same or different and which may be located in any position on the aromatic ring. Thus the benzene ring in formula I may be unsubstituted. or may have a substituent in the o, m, or p positions, or may be disubstituted at the om, op, mp, oo and/or positions.

In addition, the substituents R and R' may represent alkyl, halogen, alkyloxy, hydroxy, trifluoromethyl, or methylthio.

By the term "alkyl" is intended, in particular, a methyl radical and other simple alkyl radicals having up to 5 carbon atoms, such as ethyl, propyl, isopropyl, and the like.

The term "halogen" relates in particular to fluoro and chloro.

The term "alkoxy" refers in particular to methoxy, ethoxy and isopropoxy.

The non-toxic and pharmaceutically acceptable salts of the invention are all htose salts known to those skilled in the art which are commonly used to form salts with basic substances to be used as pharmaceutical substances, i.e., salts with monobasic or polybasic mineral acids (hydrochloric, sulfuric, phosphoric, etc.) and salts with monocarboxylic or polycarboxylic organic acids (maleic, lactic, methanesulfonic, acetic, gluconic, pamoic, etc.).

These salts are prepared by conventional techniques beginning with a pharmaceutically acceptable acid and the selected active base.

Some of these salts may be products formed by one or two molecules of acid. In addition, some of these salts may be crystallized both in the anhydrous or hydrated form and, in some cases, may retain one or more molecules of the crystallization solvent.

DESCRIPTION OF THE PREFERRED EMBODIMENTS

The compounds of the present invention may be prepared by some alternative methods, which are illustrated in the following schemes:

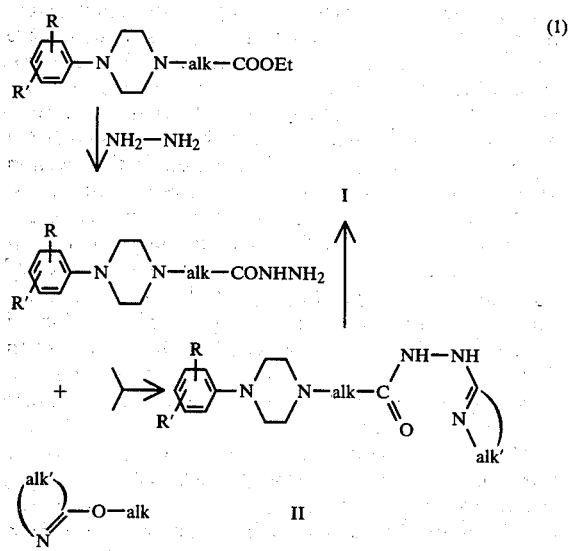

(where alk" signifies particularly methyl and ethyl)

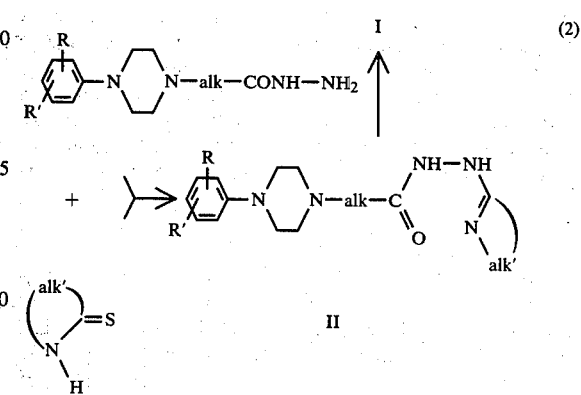

Both of the above-described methods can be applied in the preparation of all the products of the present invention.

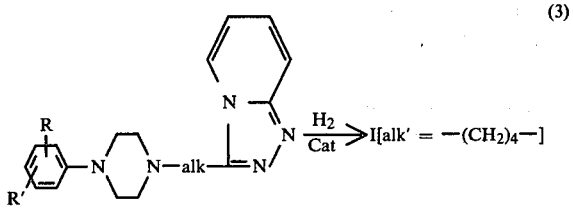

The latter method is only applicable for the preparation of tetrahydro triazole-pyridine derivatives.

In the first of said methods, there are utilized the 4-aryl-piperazinyl-alkanoic esters which are known to those skilled in the art. They are then transformed into the corresponding hydrazides with hydrazine hydrate or, in a homogeneous phase, utilizing a solvent such as ethanol or in a double phase, one of which is aqueous, using catalysts suitable for such reaction.

Alternatively, one can conduct two reactions at the same time, by directly heating the hydrazide and the lactam, either in the presence or in the absence of a solvent. In some cases, the presence of a basic catalyst, such as sodium methylate, promotes the speed of the reaction. During the heating, there is first obtained the elimination of alcohol and the formation of the amidrazone, which is not isolated, and, subsequently, the elimination of water with the closure of the triazolic ring. The reaction can be carried out either by removing the alcohol and the water which are formed in the reaction or by carrying out the reaction under reflux conditions.

The desired basic products are separated from the reaction mixture and are then salified using known techniques. In the second method there is utilized, instead of a lactam, its corresponding cyclic thioamide. Even in this case, which proceeds through the formation of hydrogen sulfide rather than alcohol, there is achieved first the formation of the amidrazone, which is not isolated, and then the elimination of water and the closure of the triazolic ring.

The third method, which is applicable only in the preparation of the derivatives of 5,6,7,8-tetrahydro-s-triazol [(4,3-a)] pyridine, begins with a 4-aryl-piperazinyl-alkanoic acid and with 2-hydrazino-pyridine. Both the 2-hydrazino-pyridine and the 4-aryl-piperazinyl-alkanoic acids are known to those skilled in the art. The two components are heated in the absence of solvent, eliminating the water which is formed during the reaction. The s-triazolo (4,3-a) -pyridine thus obtained is reduced with a selective catalyst which permits the introduction of 4 hydrogen atoms in the pyridyl ring, without removing any of the eventual substituents on the benzene ring. A catalyst which in some cases has proven to be useful in this reaction is palladium-carbon.

The following examples are illustrative of the invention:

EXAMPLE 1

Preparation of 3-[3-[4-(2-tolyl)-1-piperazinyl]propyl]-5,6,7,8-tetrahydro-s-triazolo[4,3-a]pyridine (I alk=-(CH$_2$)$_3$-; alk'=-(CH$_2$)$_4$-; R=2-CH$_3$; R'=H) A mixture of 26 g (0.147 mols) of 1-(2-tolyl)piperazine, 23 g (0.154 mols) of ethyl 4-chlorobutyrate, 11 g (0.104 mols) of anhydrous sodium carbonate and 130 ml of absolute ethanol are heated under reflux conditions, with stirring, for 24 hours.

The reaction mixture is cooled to room temperature and the sodium chloride which has been formed is removed by filtration. From the filtrate the alcohol is eliminated by heating under reduced pressure and the oily residue is distilled. There are obtained 20 g (47%) of the ethyl ester of 4-(2-tolyl)-piperazinylbutyric acid of b.p. of 185° (0.6 mm/Hg), which are dissolved in 50 ml of absolute ethanol. To this solution there is added 15 g of hydrazine hydrate (99%) and the resulting solution is refluxed for 4 hours. The alcohol is then removed under reduced pressure and the residue is taken up with 50 ml solution of 50% potassium carbonate.

The gummy residue, on standing, becomes a filtrable solid of low melting point, which is collected and washed with water and ether (14 g–74%). A small portion is transformed in the hydrochloride which shows a m.p. of 202° C. after crystallization from absolute ethanol. 14 g (0.05 mols) of the above hydrazide is mixed with 6 g (0.05 mols) of O-methylvalerolactam, to which there are added 0.4 g of dry sodium methylate and the mixture is heated, with stirring, at 120°–130° for 45–50 minutes. The mixture is cooled, and taken up in absolute ethanol. The insoluble impurities are removed by filtration and the filtrate is treated with an excess of a hydrochloric acid solution in ethanol. The precipitate which is formed is removed by filtration and recrystallized from ethanol at 95°; m.p. 266° C.; yield 16 g (73%). On analysis, the product shows the formula C$_{20}$H$_{29}$N$_5$.2HCl.H$_2$O.

EXAMPLE 2

Preparation of 3-[2-[4-(2-tolyl)-1-piperazinyl]ethyl]-6,7,8,9-tetrahydro-5H-s-triazol[4,3-a]azepine (I alk=-(CH$_2$)$_2$-; alk'=-(CH$_2$)$_5$-; R=2-CH$_3$; R'=H)

(a) Hydrazide of the 4-(2-tolyl)-piperazinyl-propionic acid

A solution of 28.4 g (0.103 mols) of the ethyl ester of 4-(2-tolyl)-piperazinyl-propionic acid and 25 g (0.5 mols) of hydrazine hydrate (99%) in 50 ml of ethanol is refluxed for 5 hours. At the end of the heating cycle the solution is cooled, it is diluted with three volumes of water and the solid hydrazide product which separates is removed by filtration and recrystallized from ethyl acetate. Yield 13.8 g (51%); m.p. 138°–139° C.

The analysis of the hydrazide product indicated the formula C$_{14}$H$_{22}$N$_4$O.

(b) A mixture formed by admixing 4.3 g (0.034 mols) of o-methylcaprolactam, 9 g (0.034 mols) of the preceding hydrazide product from (a) and 0.9 g of sodium methylate is heated, with vigorous stirring, by means of an oil bath kept at 160°–170° C. for one hour and fifteen minutes. After cooling there is extracted from the residue the portion soluble in boiling hexane by means of three successive washings and decantations. The hexane extracts are combined and evaporated to drynes. The resultant residue is dissolved in ether and there is added to it a double-equivalent quantity of a solution of hydrochloric acid in ether. The dihydrochloride which precipitates is collected by filtration and recrystallized from ethanol; m.p. 252° C.; yield 11 g (77.5%). The analysis of the hydrazide product is in agreement with the formula C$_{20}$H$_{29}$N$_5$.2HCl.

EXAMPLE 3

Preparation of 3-[2-[4-(2-tolyl)-1-piperazinyl]-ethyl]-5,6,7,8-tetrahydro-s-triazol-[4,3-a]pyridine. (I alk=-(CH$_2$)$_2$-; alk'=-(CH$_2$)$_4$-; R=2-CH$_3$; R'=H)

A mixture of 23.1 g (0.22 mols) of o-methyl valerolactam, 52.4 g (0.19 mols) of the hydrazide of 4-(2-tolyl)- piperazinyl-propionic acid and 200 ml of xylene are heated under reflux conditions removing the resultant products alcohol and the water, with a suitable apparatus which products are formed by means of azeotropic distillation. When the formation of water stops (approximately 8 hours), the resulting solution is allowed to cool and the solid which is formed is removed by filtration, washed with hexane and air dried. Yield: 41.5 g (67%); m.p. 158°–160° C. The values of the elemental analysis are in accordance to the elemental formula $C_{19}H_{27}N_5$.

Monochlorohydrate

To a solution of 3.25 g of the aforementioned base in 20 ml of absolute ethanol there is added 2 ml of a 5 N solution of HCl in ethanol. The solution is diluted with an equal volume of ethyl acetate, the solid which separates is removed by filtration and is recrystallized from absolute alcohol. Yield 3.1 g; m.p. 206°–207° C. The analysis of the chlorine ion is in agreement with the formula $C_{19}H_{27}N_5 \cdot HCl$.

Dichlorohydrate

To a solution of 3.25 of the base described above, dissolved in 20 ml of absolute ethanol, there is added 4 ml of an ethanolic solution of HCl (5 N). The resultant solid which separates is filtered and recrystallized from absolute ethanol. Yield 3.2 g, m.p. 253°–254° C.

A solution obtained by dissolving 3.25 g of the aforementioned base in 20 ml of absolute ethanol is admixed with a solution of 1.16 g of maleic acid in 10 ml of absolute ethanol. The solution is diluted with 30 ml of ethyl acetate and the solid which separates therefrom is collected by filtration and recrystallized from absolute alcohol. Yield: 2.5 g; m.p. 153°–154° C.

EXAMPLE 4

Preparation of 3-[2-[4-(3-chlorophenyl)-1-piperazinyl]-ethyl]-5,6,7,8-tetrahydro-s-triazol[4,3-a]pyridine. (I alk=-$(CH_2)_2$-; alk'=-$(CH_2)_4$-; R=3-Cl, R'=H)

(a) Preparation of hydrazide of the 4-(3-chlorophenyl)piperazinyl-propionic acid.

A solution of 14 g (0.048 mols) of the ethyl ester of 4-(3-chlorophenyl)-piperazinyl-propionic acid and 12.5 g (0.25 mols) of hydrazine hydrate (99%) in 20 ml of ethanol is refluxed for 4 hours.

From the final solution the alcohol is removed under reduced pressure, and the residue is taken up with water and the oil which separates is extracted with chloroform. The residue which is obtained when the chloroform is removed is recrystallized from an hexaneethyl acetate mixture. Yield: 13 g (98%); m.p. 110°–112° C. The elemental analysis results in agreement with the formula $C_{13}H_{19}ClN_4O$.

(b) A mixture of 2.5 g (0.022 mols) of 2-thiopiperidone, 5.4 g (0.019 mols) of the above hydrazide and 0.1 g of dry sodium methylate are heated, with stirring, at 120°–130° C. for 4 hours.

At the end of the heating period, the residue is taken up in water, the solid thus obtained is filtered and, after air drying, is dissolved in absolute alcohol.

To this solution there is added an excess of an ethanolic HCl solution and the solid which precipitates is collected by filtration and recrystallized from absolute ethanol. Yield: 6 g (75%); m.p. 211° C. The elemental analysis indicates a formula of $C_{18}H_{24}ClN_5 \cdot 2HCl$

EXAMPLE 5

Preparation of 3-[2-[4-(2-tolyl)-1-piperazinyl]-ethyl]-5,6,7,8-tetrahydro-s-triazol-[4,3-a]pyridine (I alk=-$(CH_2)_2$-; alk'=-$(CH_2)_4$-; R=2-$CH_3$; R'=H)

(a) Hydrazide of the 4-(2-tolyl)-piperazinyl-propionic acid with the 3,4,5,6-tetrahydro-2-hydrazino-pyridine.

To a solution of 8 g (0.07 mols) of O-methyl-valerolactam in 120 ml of benzene there is added 17.5 g (0.067 mols) of hydrazide of the 4-(2-tolyl)-piperazinyl-propionic acid. The suspension is vigorously stirred for 3 hours at room temperature.

(b) 18 g (0.053 mols) of the above amidrazone are suspended in 200 ml of benzene. The mixture is refluxed for 3 hours, removing the water which is formed azeotropically. At the end of heating cycle the mixture is cooled, the solid which is formed is removed by filtration and recrystallized from benzene. Yield: 15 g (88%); m.p. 161°–162° C.

EXAMPLE 6

With one of the methods described in Examples 1–4 there have been prepared:

3-[2-[4-(2.5-dichlorophenyl)-1-piperazinyl]-ethyl]-6,7,8,9-tetrahydro-5H-s-triazol[4,3-a]azepine (I alk=-$(CH_2)_2$-; alk'=-$(CH_2)_5$-; R=2-Cl; R'=5 Cl)

Monochlorohydrate. $H_2O$ m.p. 220° C. (from alcohol at 95° C.)

The hydrazide of the 4-(2.5-dichlorophenyl)-piperazinyl-propionic acid, necessary for the synthesis of said product, was prepared by the previously described method, and has a m.p.=135°–137° C. (from ethyl acetate). The ethyl ester of the 4-(2.5-dichlorophenyl)-piperizinyl-propionic acid, necessary for the synthesis of the preceding hydrazide, was prepared by the described method and has a b.p. of 198°–200° C./1 mm.

Dichlorohydrate. $H_2O$ m.p.=218° C. (from alcohol at 95° C.)

3-[2-[4-(3-chlorophenyl)-1-piperazinyl]-ethyl]-6,7,8,9-tetrahydro-5H-s-triazol[4,3-a]azepine (I alk=-$(CH_2)_2$-; alk'=-$(CH_2)_5$-; R=3-Cl; R'=H) Chlorohydrate m.p. 234° C. (from absolute ethanol)

3-[3-[4-(2-tolyl)-1-piperazinyl]-propyl]-6,7,8,9-tetrahydro-5H-s-triazol-[4,3-a]azepine. (I alk=-$(CH_2)_3$-; alk'=-$(CH_2)_5$-; R=2-$CH_3$; R'=H) Monochlorohydrate m.p. 271° C. (from absolute ethanol).

3-[2-[4-(2-methoxyphenyl)-1-piperazinyl]-ethyl]-6,7,8,9-tetrahydro-5H-s-triazol[4,3-a]azepine (I alk=-$(CH_2)_2$-; alk'=-$(CH_2)_5$-; R=2-$OCH_3$; R'=H) Monochlorohydrate m.p. 230° C. (from absolute ethanol).

EXAMPLE 7

Preparation of 3-[2-[4-(2-tolyl)-1-piperazinyl]-ethyl]-5,6,7,8-tetrahydro-s-triazol[4,3-a]pyridine (I alk=-$(CH_2)_2$-; alk'=-$(CH_2)_4$-; R=2-$CH_3$; R'=H) by the reduction of the 3-[2-[4-(2-tolyl)-1-piperazinyl]-ethyl]-s-triazol[4,3-a]pyridine.

(a) Preparation of the 4-(2-tolyl)-piperazinyl-propionic acid. 31 g (0.135 mols) of 4-(2-tolyl)piperazinyl propionitrile are dissolved in a solution of 8.4 g (0.150 mols) of KOH in 250 ml of 60% ethanol. The solution is refluxed for 4 hours and the ethanol is then removed under reduced pressure.

20 g (0.071 mols) of the above chlorohydrate are suspended in 80 ml of water, there are added 3.4 g (0.085 mols) of NaOH in pellet form and the mixture is stirred at room temperature for one hour.

(b) Preparation of the 3-[2-[4-(2-tolyl)-1-piperazinyl]-ethyl]-s-triazol-[4,3-a]pyridine. 85.0 g (0.34 mols) of 4-(2-tolyl)piperazinyl-propionic acid and 35.0 g (0.32 mols) of 2-hydrazino-pyridine are heated with stirring for 3 hours at 160° C.

(c) A solution of 15 g (0.038 mols) of the above chlorohydrate, dissolved in 750 ml of ethanol at 95° C. is hydrogenated in a Parr shaker at an initial pressure of 3 atmospheres using 1.5 g of a palladium-carbon catalyst. The melting point of the product is 216°–218° C., even when mixed with a sample of the dichlorohydrate monohydrate obtained according to Example 3. Yield: 13 g (82%).

EXAMPLE 8

As indicated above, the compounds of the present invention, administered in effective amounts, are effective in treating:

(a) the hypertensive states of the eye, including glaucoma, when administered topically or systemically;

(b) psychopathological symptoms of the psychosis of the schizophrenic type, with particular reference to hallucinations and to the delirium, by means of oral or parental administration; and (c) the abstinence syndromes in patients with states of psychophysical addiction or dependence produced by alcohol, smoking or pharmaceutical substances, by means of oral or parental administration.

In the latter states (c) there is not realized a substitutive treatment for other forms of treatment presently used, but the abstinence syndrome is alleviated by acting on the physiological mechanisms which cause it. The present compounds, therefore, may be considered as adjuvant or supplemental agents which may be used in conjunction with other forms of therapy, such as psychotherapy, in order to facilitate the withdrawal process.

The therapeutic value of the compounds of the present invention for each of the utilities described has been determined by the use of experimental models which demonstrate the effect on each of the various symptoms indicated above.

The ability to reduce the ocular pressure has been studied both in the normal rabbit, utilizing experimental conditions already described (Burberi et al, "Effects of systemically administered drugs on intraocular pressure in rabbits", Arzneim. Forsch., 20, 1143–1147 (1970); De Feo et al, "Effects of topically instilled drugs on intraocular pressure in rabbits", Arnzeim. Forsch., 25, 806–809 (1975)) and in animals with ocular hypertension.

An example of ocular hypertension used in the tests is that which has been obtained by introducing repeatedly in one of the two eyes of rabbit a suspension of betametasone. It is thus possible to obtain a stable ocular hypertension which cannot be distinguished from human glaucoma.

The test products have been shown to reduce the ocular pressure in the normal rabbit and in the rabbit with ocular hypertension, both when administered topically, in the form of eye wash at 0.25–0.5% concentration, and when administered parentally at doses between 0.1–1 mg/kg i.v.

In ocular hypertension the new products have been compared to pilocarpine, in the form of eyewash in 0.5–1% concentration and have proven to be equally active. With respect to the latter product, however, they have the advantage of not producing miosis and other irritations.

In addition, the products have shown an activity similar to that of the neuroleptics in the common laboratory test used for the studies of this class of pharmaceuticals.

By way of example, similar methods were used as those for amphetamine toxicity in mice (Lagerspetz et al, "Amphetamine toxicity in genetically aggressive and non-aggressive mice", J. Pharm. Pharmacol., 23, 542 (1971)).

The products have been compared with chlorpromazine and have shown an activity similar to this compound.

With respect to chlorpromazine and to the other traditional neuroleptic agents, the products of the present invention present two basic advantages consisting of lower toxicity and of a lack of catathony.

On the basis of these last indications, the present compounds may be considered free of the side effects of the extrapyramidal type which are a common characteristic of the other neuroleptics.

Finally, the tests which have led to the use of the present compounds in the treatment of addition or habituation to alcohol, to smoking and to some habit-forming pharmaceuticals substances, have been conducted utilizing a completely new operational theory.

It is known that addition or dependence on alcohol or on other substances are considered manifestations of psychological adaptations which the organism develops to compensate for the depressing effects of these substances. When the administration of these substances is interrupted, the adaptations effected by the organism are no longer counterbalanced by the opposite effects of the substances and consequently there appear the symptoms of the withdrawal reaction.

To verify this theory, there has been produced, in test animals, a syndrome of addiction or dependence to the following substances: alcohol, nicotine, morphine and clonidine.

The results obtained show that the abstinence syndromes which result when the above treatments are interrupted may be treated not only with alternate treatments which vary from case to case (i.e., lobeline is active only in the case of nicotine, while the methadone is active only in case of the morphine), but also with substances which act non-specifically in all the above-mentioned types of abstinence syndromes. These substances are those of the present invention and are the only ones, of the numerous products studied, which possess this property. They may thus be utilized as supplemental agents in the withdrawal treatment of patients with addiction or dependence of various natures utilizing a totally new mode of action.

In fact, the new substances seem to act on a physiological system which the organism uses to counterbalance the depressing effect of substances such as alcohol and morphine. In this manner it is possible to fight the abstinence symptoms not through subsitutive therapy, which often is equally dangerous as the agent which has produced the addiction (such as in the case of methadone used in the treatment of addiction to morphine or to other drugs), but acting directly on the physiological system which is responsible for the abstinence syndrome.

The therapeutic treatments follow the following regime of use: orally, the products are administered at a medium dosage of 25–50 mg three times a day. In the treatment of schizophrenia and other psycotic forms, as well as in the treatment of particularly serious abstinence syndromes, the dosages used may reach 200 mg three times a day.

For oral administration, there may be used any type of oral non-toxic formulation, which is commonly used, such as solutions, suspensions, tablets, capsules, powders, show-release formulations and the like.

For parental administration, the products may be administered at the medium dosage of 25-50 mg, 2 or 3 times a day.

In the treatment of glaucoma and of other hypertensive ocular forms the products are administered in the form of eyewash (concentration 0.25-0.5%) from 2 to 4 times a day. To this effect there may be utilized an aqueous or oily formulation chosen among those which are commonly used in the optical field.

In addition, the compounds of the present invention may be administered at the same time with other pharmaceutical agents, bearing in mind the particular type of disease being treated.

While specific embodiments of the invention have been shown and described in detail to illustrate the application of the principles of the invention, it will be understood that the invention may be embodied otherwise without departing from such principles.

What is claimed is:

1. A method of treating symptoms of schizophrenia comprising, administering to a patient having symptoms of schizophrenia an amount of a compound of the formula I or its pharmaceutically acceptable salt which is sufficient to remove said symptoms from the patient, said formula I being:

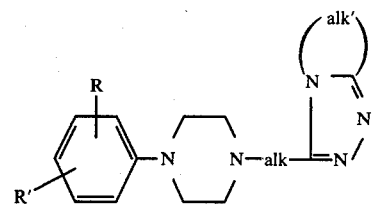

wherein "alk" is selected from the group consisting of linear and branched divalent aliphatic chains having from 1 to 10 carbon atoms; "alk'" is selected from the group consisting of linear and branched divalent aliphatic chains having from 1 to 5 carbon atoms; and each R and R' is selected from the group consisting of hydrogen, alkyl having from 1 to 5 carbon atoms, halogen, alkyloxy having from 1 to 3 carbon atoms, hydroxy, trifluormethyl and methylthio.

2. A method of treatment according to claim 1, wherein the compound is 3-[3-[4-(2-tolyl)-1-piperazinyl]propyl]-5,6,7,8-tetrahydro-s-triazol [4,3a] pyridine.

3. A method of treatment according to claim 1, wherein the compound is 3-[2-[4-(2-tolyl)-1-piperazinyl]ethyl]-6,7,8,9-tetrahydro-5H-s-triazol [4,3a] azepine.

4. A method of treatment according to claim 1, wherein the compound is 3-[2-[4-(2-tolyl)-1 piperazinyl]-ethyl]-5,6,7,8-tetrahydro-s-triazol-[4,3-a]pyridine.

5. A method of treatment according to claim 1, wherein the compound is 3-[2-[4-(3-chloro-phenyl)-1-piperazinyl]-ethyl]-5,6,7,8-tetrahydro-s-triazol [4,3-a] pyridine.

6. A method of treatment according to claim 1, wherein the compound is 3-[2-[4-(2-tolyl)-1-piperazinyl]-propyl]-6,7,8,9-tetrahydro-5H-s-triazol-[4,3-a]azepine.

7. A method of treatment according to claim 1, wherein the compound is 3-[2-[4-(2,5-di-chlorophenyl)-1-piperazinyl]-ethyl]-6,7,8,9-tetrahydro-5h-s-triazol [4,3-a] azepine.

8. A method of treatment according to claim 1, wherein the compound is 3-[2-[4-(2-methoxyphenyl-1-piperazinyl]-ethyl]-6,7,8,9 tetrahydro-5H-s-triazol [4,3-a]-azepine.

* * * * *